(12) United States Patent
Frisch (10) Patent No.: US 10,180,511 B2
(45) Date of Patent: Jan. 15, 2019

(54) PEAK ANALYSIS OF ULTRASONIC WAVEFORMS FOR CEMENT BOND LOGGING

(71) Applicant: Halliburton Energy Services, Inc., Houston, TX (US)

(72) Inventor: Gary James Frisch, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/782,431

(22) PCT Filed: May 19, 2015

(86) PCT No.: PCT/US2015/031564
§ 371 (c)(1),
(2) Date: Oct. 5, 2015

(87) PCT Pub. No.: WO2016/003549
PCT Pub. Date: Jan. 7, 2016

(65) Prior Publication Data
US 2017/0108607 A1 Apr. 20, 2017

Related U.S. Application Data

(60) Provisional application No. 62/020,121, filed on Jul. 2, 2014.

(51) Int. Cl.
*G01V 1/50* (2006.01)
*G01N 29/11* (2006.01)
(Continued)

(52) U.S. Cl.
CPC ............ *G01V 1/50* (2013.01); *E21B 47/0005* (2013.01); *E21B 47/124* (2013.01); *G01N 29/11* (2013.01);
(Continued)

(58) Field of Classification Search
CPC .......... G01V 1/50; E21B 33/14; E21B 33/00; E21B 2033/105; E21B 47/0005; G01N 29/11; G01N 29/48
See application file for complete search history.

(56) References Cited

U.S. PATENT DOCUMENTS

| | | |
|---|---|---|
| 5,907,131 A | 5/1999 | Tello |
| 2005/0190648 A1 | 9/2005 | Tang et al. |

(Continued)

FOREIGN PATENT DOCUMENTS

| | | |
|---|---|---|
| GB | 2059064 A | 4/1981 |
| WO | WO 1999/031354 A1 | 6/1999 |
| WO | WO-2010121158 A2 | 10/2010 |

OTHER PUBLICATIONS

Frisch et al., Advances in Cement Evaluation Tools and Processing Methods Allow Improved Interpretation of Complex Cements, Oct. 9-12, 2005, 2005 SPE Annual Technical Conference and Exhibition, Dallas, TX, SPE 97186, 13 pp.*

(Continued)

*Primary Examiner* — Toan Le
(74) *Attorney, Agent, or Firm* — Haynes and Boone, LLP (57) ABSTRACT

A cement bond log from recorded ultrasonic waveforms, a method for evaluating bonding of cement in a wellbore between a casing and a wellbore wall, and a method for creating a cement bond log from recorded ultrasonic waveforms are disclosed, in which series of points corresponding to maxima and minima of the waveforms are identified. Absolute value amplitudes of the series of points are thereafter identified and a correlation thereof is analyzed to divide each series of points into four or more zones, corresponding to casing arrival data, inner and outer annular data, wellbore wall arrival data, respectively. Mean values of the absolute value amplitudes of the waveforms for points of each series (Continued)

falling within each of the four zones are calculated, which relate to cement bonding at the depths of the recorded ultrasonic waveforms.

14 Claims, 11 Drawing Sheets

(51) Int. Cl.
  *E21B 47/00* (2012.01)
  *E21B 47/12* (2012.01)
  *G01N 29/48* (2006.01)
  *E21B 33/14* (2006.01)

(52) U.S. Cl.
  CPC .............. *G01N 29/48* (2013.01); *E21B 33/14* (2013.01); *G01N 2291/0232* (2013.01); *G01N 2291/267* (2013.01)

(56) References Cited

U.S. PATENT DOCUMENTS

2007/0131417 A1  6/2007  Bolshakov et al.
2008/0112262 A1  5/2008  Tang et al.

OTHER PUBLICATIONS

Kessler et al., Cement-Bond Evaluation: A Step Change in Capabilities, 2011, SPE 145970, 15 pp.*
International Search Report and Written Opinion, dated Aug. 21, 2015, 10 pages; Korean International Searching Authority.
Search Report issued for European Patent Application No. 15814382.6, dated Mar. 28, 2018, 9 pages.

* cited by examiner

PEAK ANALYSIS OF ULTRASONIC WAVEFORMS FOR CEMENT BOND LOGGING

CROSS-REFERENCE TO RELATED APPLICATIONS

The present application is a U.S. National Stage patent application of International Patent Application No. PCT/US2015/031564, filed on 19May 2015, which claims the benefit and priority of U.S. Provisional Application 62/020,121filed on 2Jul. 2014; the benefits of each are claimed and the disclosures of each are incorporated herein by reference in their entirety.

TECHNICAL FIELD

The present disclosure relates generally to oilfield equipment, and in particular to downhole tools, drilling systems, and drilling techniques for drilling wellbores in the earth. More particularly still, the present disclosure relates to logging systems and methods for evaluating bonding of cement in a wellbore between a casing and a wellbore wall.

BACKGROUND

The use of the both sonic and ultrasonic waveforms have been used to evaluate the quality of the cement sheath between the casing wall and formation. A logging tool, which may have one or more sonic and/or ultrasonic receivers and one or more sonic and/or ultrasonic transmitters, is lowered into a wellbore and measurements are taken at various depths. Sonic and/or ultrasonic waves are transmitted from the logging tool in the wellbore, and reflected waves from the casing, cement, and formation are received, recorded, processed, and interpreted to determine the presence, or lack thereof, of cement between the casing and the formation or other wellbore wall.

BRIEF DESCRIPTION OF THE DRAWINGS

Embodiments are described in detail hereinafter with reference to the accompanying figures, in which.

DETAILED DESCRIPTION

The present disclosure may repeat reference numerals and/or letters in the various examples. This repetition is for the purpose of simplicity and clarity and does not in itself dictate a relationship between the various embodiments and/or configurations discussed. Further, spatially relative terms, such as "beneath," "below," "lower," "above," "upper," "uphole," "downhole," "upstream," "downstream," and the like, may be used herein for ease of description to describe one element or feature's relationship to another element(s) or feature(s) as illustrated in the figures. The spatially relative terms are intended to encompass different orientations of the apparatus in use or operation in addition to the orientation depicted in the figures.

Recorded sonic waveforms, commonly referred to as cement bond log, variable display log or micro seismogram log data, may be plotted with respect to wellbore depth and then visually interpreted by an operator to provide a basic understanding of the composition of the cement sheath in the annular space. Cement bond log data may be plotted with arrival time indicated horizontally, wellbore depth indicated vertically, and waveform amplitude indicated by color or intensity, resulting in a serrated or striped display. Adjacent to this cement bond log plot, a waveform amplitude plot and a gamma ray plot may be provided for correlation.

Waveforms have a completely different signature when the annular space is filled with fluid (free pipe) or solid (cement). The free pipe signature includes higher amplitudes, a low rate of attenuation and a consistent waveform. When the annular space is filled with a solid material the amplitude of the waveform is reduced, the attenuation of the same waveform is increased, and the waveforms are not consistent.

In other words, there is typically a significant visible difference in the plotted sonic waveform data between a free pipe response and bonded pipe response. Free pipe is indicated by high waveform amplitude, strong casing arrival, straight or consistent waveforms with depth (indicated by regular striping with depth as plotted), and visible chevron patterns at casing joints. A good cement sheath is indicated by attenuated waveform amplitude, weak casing arrival, and inconsistent waveforms with depth (indicated by irregular striping with depth as plotted), which may correspond with the gamma ray plot.

However, interpretation of a partial cement bond, such as the presence of either a channel, mixed cement and drilling fluids, spacers, or a combination thereof, can be more difficult. There is an apparent transition zone between good and poor cement bonds, and identification of and analysis of the bond in such cases relies on the experience and eyes of the analyst to assess if the cement sheath is adequate for continued wellbore completion operations or if remedial work is required.

In addition to the analysis of sonic waveforms, ultrasonic waveform may be used to evaluate the cement sheath by determining either the impedance or attenuation of the material next to the casing itself. The impedance and attenuation of the material is normally mathematically calculated using properties of the casing, cement, mud and other materials in a complicated method requiring extensive knowledge of a routineer in the field.

The use of use of the sonic and ultrasonic analysis techniques described above may be combined with a peak analysis method described below to provide the analyst with a cement bond log that is easy to visually understand an interpret and that provides detailed information about the composition of the annular wellbore region.

Figure 1:
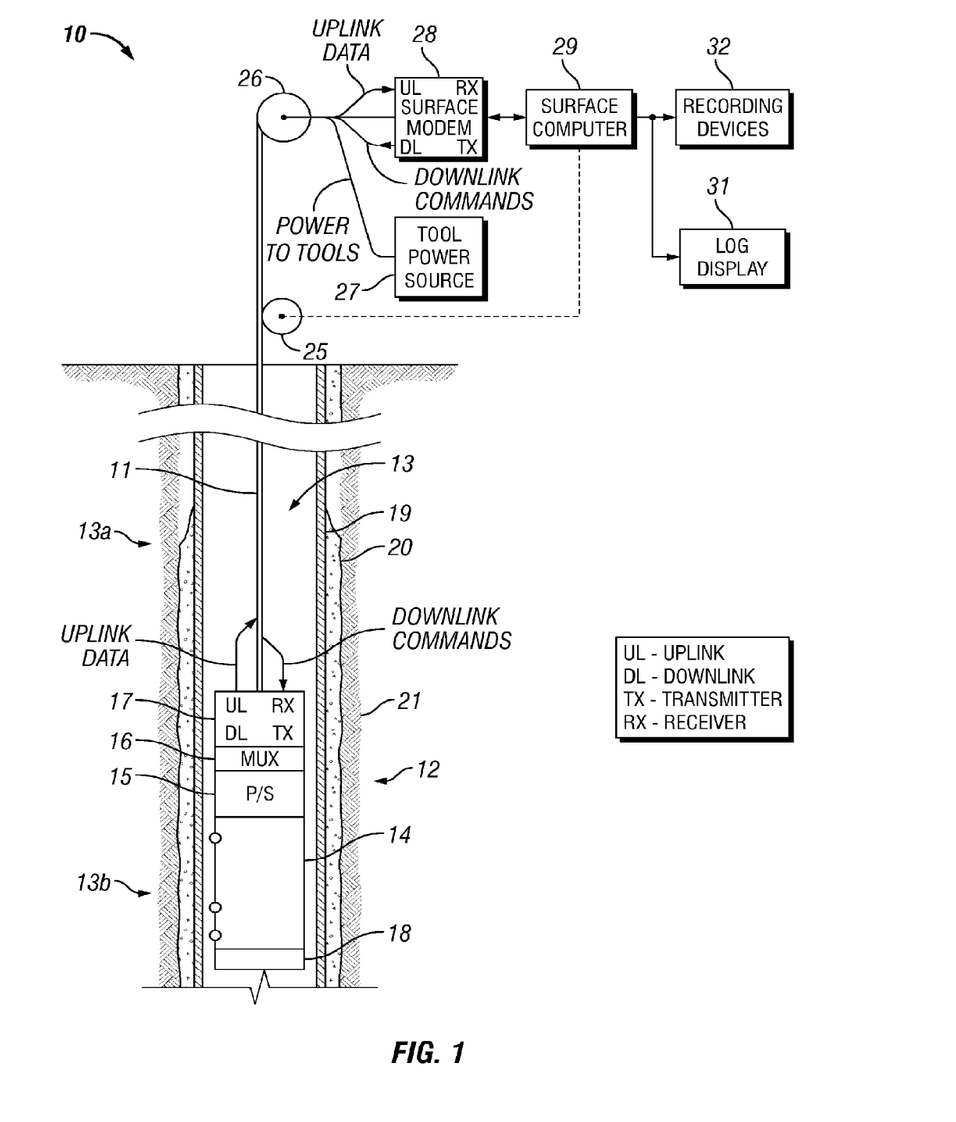
FIG. 1 is a block-level schematic diagram of a well logging system according to an embodiment, showing a logging tool suspended by wireline in a well and incorporating a cement bonding logging tool, such as that of FIG. 3.

FIG. 1 shows a system view of a well logging system of the present disclosure. The system shown in FIG. 1 is identified by the numeral 10 which generally refers to a well logging system.

Figure 2:
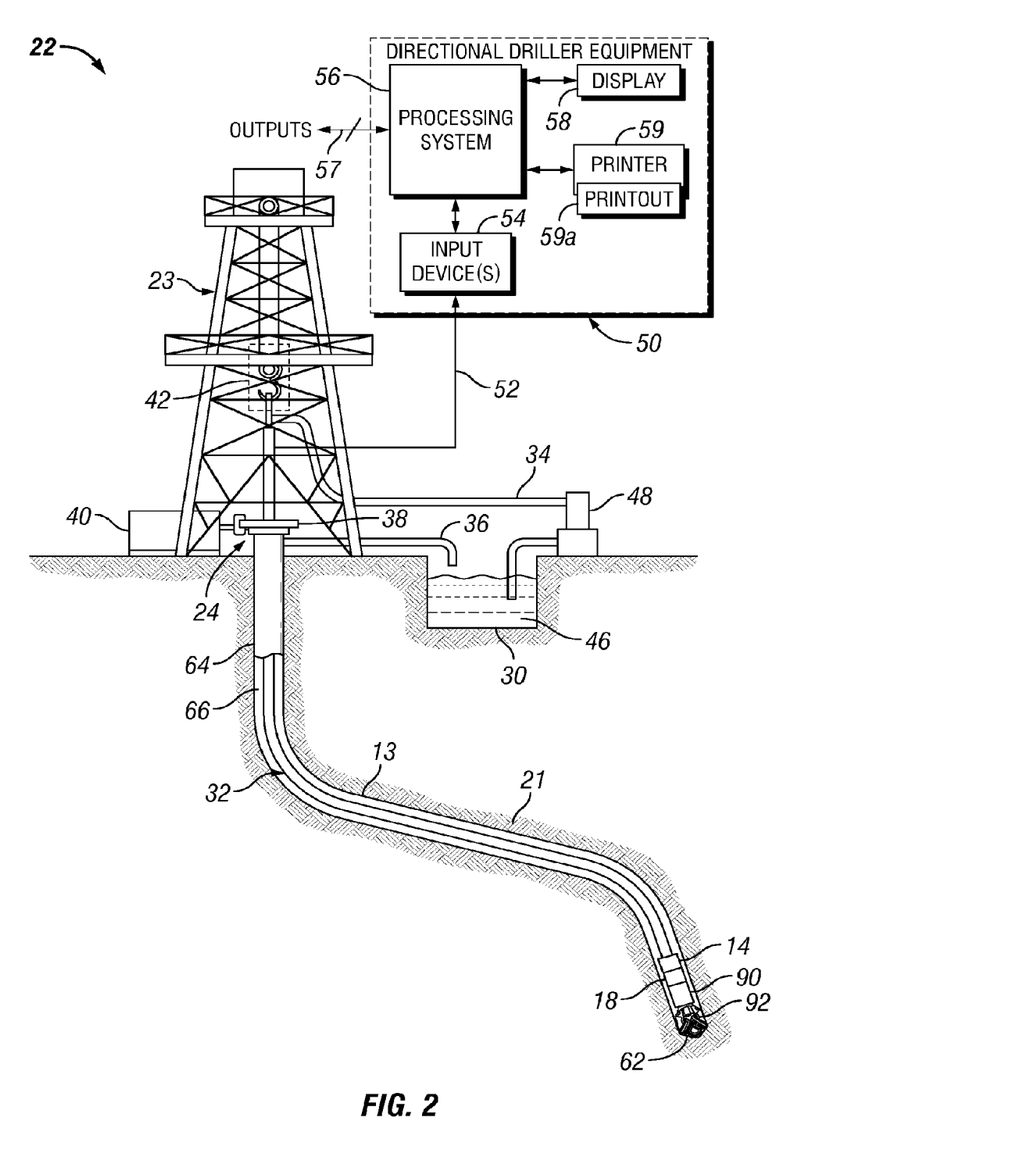
FIG. 2 is a block-level schematic diagram of a logging while drilling system according to an embodiment, showing a drill string and a drill bit for drilling a bore in the earth and a logging tool disposed in a drill string incorporating a cement bonding logging tool, such as that of FIG. 3.

A logging cable 11 suspends a sonde 12 in a wellbore 13. Wellbore 13 may drilled by a drill bit on a drill string as illustrated in FIG. 2, and wellbore 13 may be lined with casing 19 and a cement sheath 20. Wellbore 13 can be any depth, and the length of logging cable 11 is sufficient for the depth of wellbore 13. For illustrative purposes, a shallow portion 13a of wellbore 13 lacks a cement bond, while a deeper portion 13b of wellbore 13 has a good cement bond.

Sonde 12 generally has a protective shell or housing which is fluid tight and pressure resistant and which enables the equipment on the interior to be supported and protected during deployment. Sonde 12 encloses one or more logging tools which generate data useful in analysis of wellbore 13 or in determining the nature of the formation 21 in which wellbore 13 is located.

In one embodiment, a cement bonding logging tool 14 is provided, as described below with respect to FIG. 3, for testing the quality of the bond of cement 20 with the exterior of wellbore casing 19 and formation 21, for example. Other types of tools may also be included in sonde 12, such as a gamma ray tool 18. Sonde 12 may also enclose a power supply 15. Output data streams from cement bonding logging tool 14 and gamma ray tool 18 may be provided to a multiplexer 16 located in sonde 12. Sonde 12 may also include a communication module 17 having an uplink communication device, a downlink communication device, a data transmitter, and a data receiver.

Logging system 10 includes a sheave 25 which is used in guiding the logging cable 11 into wellbore 13. Cable 11 is spooled on a cable reel 26 or drum for storage. Cable 11 connects with sonde 12 and is spooled out or taken in to raise and lower sonde 12 in wellbore 13. Conductors in cable 11 connect with surface-located equipment, which may include a DC power source 27 to provide power to tool power supply 15, a surface communication module 28 having an uplink communication device, a downlink communication device, a data transmitter and also a data receiver, a surface computer 29, a logging display 31 and one or more recording devices 32. Sheave 25 may be connected by a suitable means to an input to surface computer 29 to provide sonde depth measuring information. The surface computer 29 may provide an output for a logging display 31 and a recording device 32. The surface logging system 10 may collect data as a function of depth. Recording device 32 is incorporated to make a record of the collected data as a function of depth in wellbore 13.

FIG. 2 illustrates a system view of a measurement while drilling (MWD) or logging while drilling (LWD) system of the present disclosure. The system shown in FIG. 2 is identified by the numeral 22 which generally refers to a drilling system.

LWD system 22 may include land drilling rig 23. However, teachings of the present disclosure may be satisfactorily used in association with offshore platforms, semi-submersible, drill ships and any other drilling system satisfactory for forming wellbore 13 extending through one or more downhole formations.

Drilling rig 23 and associated control system 50 may be located proximate well head 24. Drilling rig 23 generally also includes rotary table 38, rotary drive motor 40 and other equipment associated with rotation of drill string 32 within wellbore 13. Annulus 66 is formed between the exterior of drill string 32 and the inside diameter of wellbore 13.

For some applications drilling rig 23 may also include top drive motor or top drive unit 42. Blow out preventers (not expressly shown) and other equipment associated with drilling a wellbore 13 may also be provided at well head 24. One or more pumps 48 may be used to pump drilling fluid 46 from fluid reservoir or pit 30 to one end of drill string 32 extending from well head 24. Conduit 34 may be used to supply drilling fluid from pump 48 to the end of drilling string 32 extending from well head 24. Conduit 36 may be used to return drilling fluid, reservoir fluids, formation cuttings and/or downhole debris from the bottom or end 62 of wellbore 13 to fluid reservoir or pit 30. Various types of pipes, tube and/or conduits may be used to form conduits 34 and 36.

Drill string 32 may extend from well head 24 and may be coupled with a supply of drilling fluid, such as pit or reservoir 30. The opposite end of drill string 32 may include bottom hole assembly 90 having a rotary drill bit 92 disposed adjacent to end 62 of wellbore 13. Bottom hole assembly 90 may also include bit subs, mud motors, stabilizers, drill collars, or similar equipment. Rotary drill bit 92 may include one or more fluid flow passageways with respective nozzles disposed therein. Various types of drilling fluids 46 may be pumped from reservoir 30 through pump 48 and conduit 34 to the end of drill string 32 extending from well head 24. The drilling fluid 46 may flow through a longitudinal bore (not expressly shown) of drill string 32 and exit from nozzles formed in rotary drill bit 92.

At end 62 of wellbore 13 drilling fluid 46 may mix with formation cuttings and other downhole fluids and debris proximate drill bit 92. The drilling fluid will then flow upwardly through annulus 66 to return formation cuttings and other downhole debris to well head 24. Conduit 36 may return the drilling fluid to reservoir 30. Various types of screens, filters and/or centrifuges (not expressly shown) may be provided to remove formation cuttings and other downhole debris prior to returning drilling fluid to pit 30.

Bottom hole assembly 90 or drill string 32 may also include various tools that provide logging or measurement data and other information about wellbore 13. This data and information may be monitored by a control system 50. In particular, cement bonding logging tool 14 may be provided, as described below with respect to FIG. 3. Additionally, other various types of MWD or LWD tools may be included, such as gamma ray tool 18.

Measurement data and other information may be communicated from cement bonding logging tool 14 and gamma ray tool 18 through fluid within drill string 32 or annulus 66 using MWD techniques and converted to electrical signals at the surface. Electrical conduit or wires 52 may communicate the electrical signals to input device 54. The measurement data provided from input device 54 may then be directed to a data processing system 56. Various displays 58 may be provided as part of control system 50.

For some applications printer 59 and associated printouts 59 may also be used to monitor the performance of drilling string 32, bottom hole assembly 90 and associated rotary drill bit 100. Outputs 57 may be communicated to various components associated with operating drilling rig 22 and may also be communicated to various remote locations to monitor the performance of drilling system 22.

Figure 3:
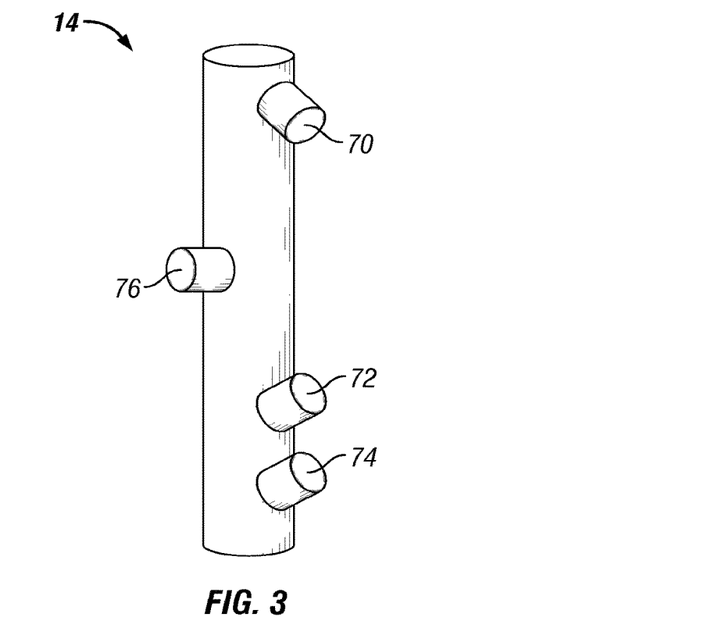
FIG. 3 is a perspective view of a cement bonding logging tool according to an embodiment.

FIG. 3 is a perspective view of cement bonding logging tool 14 according to an embodiment. Referring to FIG. 3, cement bonding logging tool 14 may include a source transmitter 70 and two or more receivers 72, 74, which may be arranged in a pitch and catch configuration. That is, source transmitter 70 may be a pitch transducer, and receivers 72, 74 may be near and far catch transducers spaced at near and far axial distances from source transmitter 70, respectively. In such a configuration, source pitch transducer 70 emits sonic or ultrasonic waves while near and far catch transducers 72, 74 receive the sonic or ultrasonic waves after reflection from the wellbore casing, cement and formation. Because the distance between near catch transducer 72 and far catch transducer 74 is known, differences between the reflected waveforms received at each catch sensor 72, 74 provide information about attenuation, which can be correlated to the material in the annular wellbore region, and allow a circumferential depth of investigation around the wellbore.

The pitch-catch transducer pairing may have different frequency, spacing, and/or angular orientations based on environmental effects and/or tool design. For example, if transducers 70, 72, 74 operate in the sonic range, spacing ranging from three to 15 feet may be appropriate, with three and five foot spacing being common. If transducers 70, 72, 74 operate in the ultrasonic range, the spacing would be less.

Cement bonding logging tool 14 may include, in addition or as an alternative to transducers 70, 72, 74, a pulsed echo ultrasonic transducer 76. Pulsed echo ultrasonic transducer 76 may operate at a frequency from 80kHz up to 800kHz, for example. The optimal transducer frequency is a function of the casing size, weight, mud environment and other conditions. Pulsed echo ultrasonic transducer 76 generates and then receives for recording the same energy in a mode of a waveform.

Figure 4:
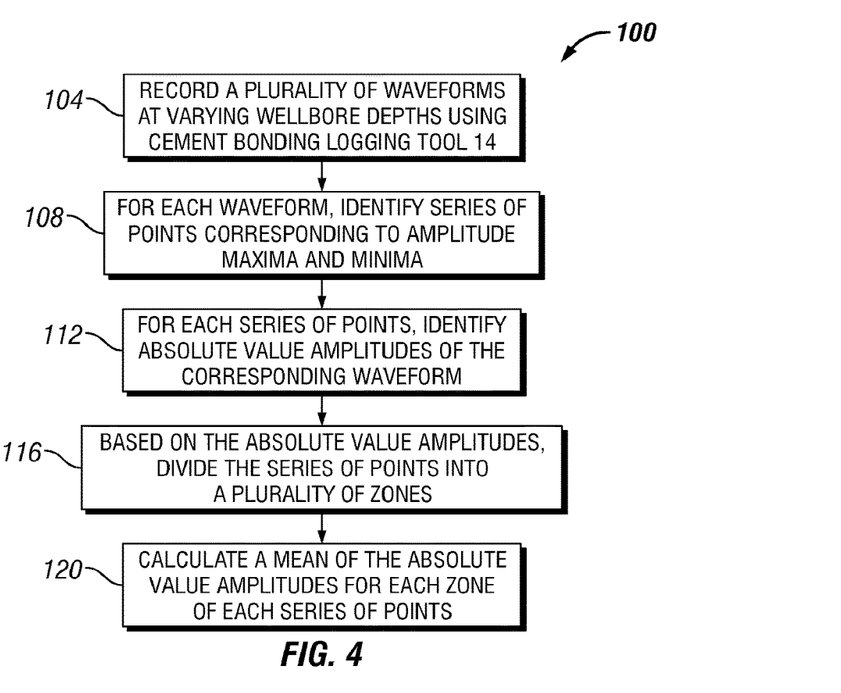
FIG. 4 is a basic flow chart of a method for evaluating bonding of cement in a wellbore and creating a cement bond log according to one or more embodiments of the invention.

FIG. 4 is a basic flow chart of a peak analysis method 100 for evaluating bonding of cement in a wellbore and creating a cement bond log according to one or more embodiments of the invention. Peak analysis method 100 may be applied to pulse echo ultrasonic waveforms and/or sonic or ultrasonic pitch and catch waveforms from cement bonding logging tool 14 (FIG. 3), either in conjunction with logging system 10 (FIG. 1) or drilling system 22 (FIG. 2). That is, peak analysis method 100 can use standard sonic, pulse echo ultrasonic, and/or pitch and catch ultrasonic waveforms and process such waveforms, regardless of the waveform type or method of generation, using identified peaks and troughs to determine the type and characteristic of the material in the wellbore annular space. Peak analysis method 100 is a visual method to determine cement placement in the wellbore annular space, not only near the casing wall, but also in areas away from the casing wall, which have historically been difficult to evaluate.

Figure 5A:
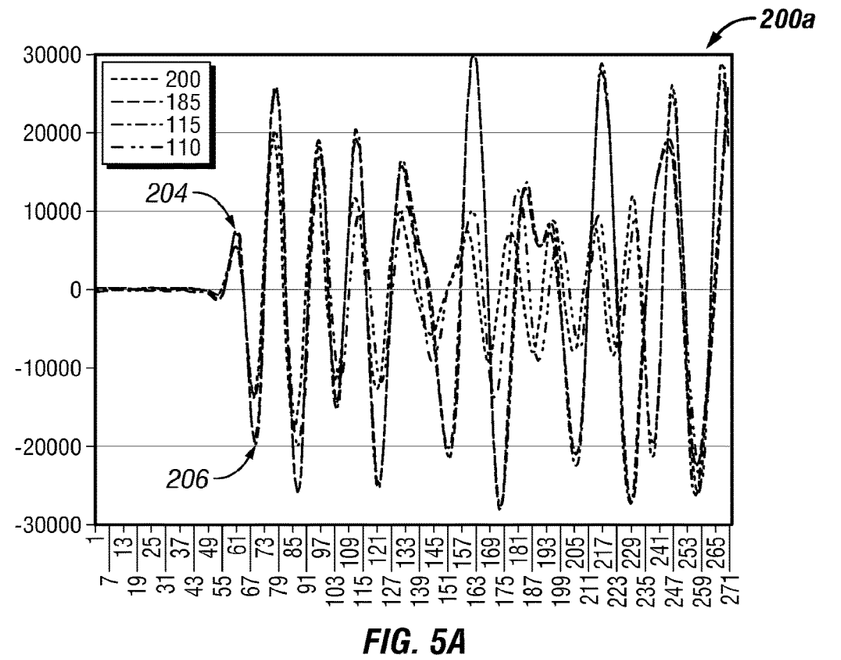
FIG. 5A is a graph of four recorded waveforms at four different depths taken in a shallower section of the wellbore of FIG. 1 characterized by free, or unbonded, pipe.
Figure 5B:
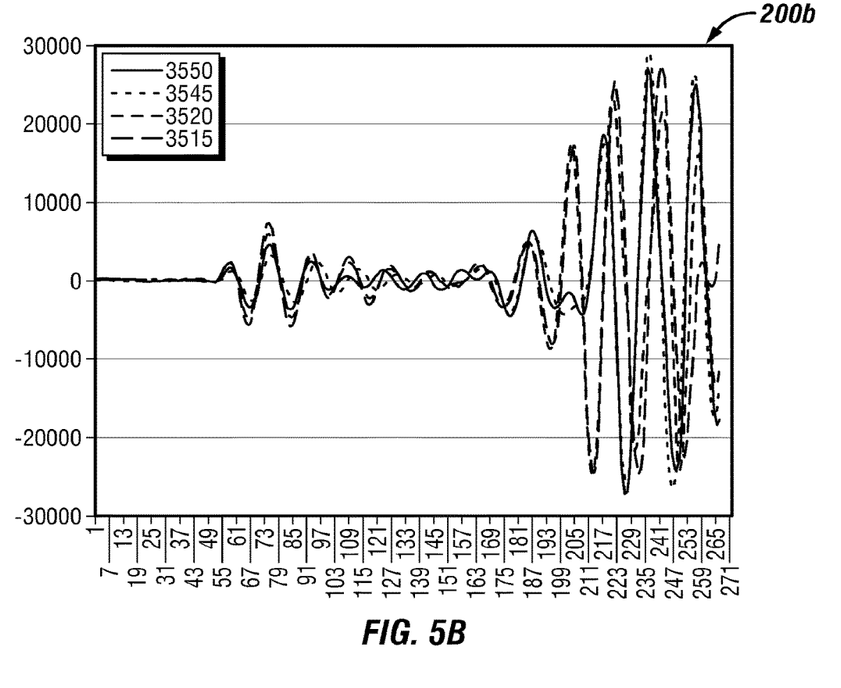
FIG. 5B is a graph of four recorded waveforms at four different depths taken in a deeper section of the wellbore of FIG. 1 characterized by bonded pipe.

For illustration of peak analysis method 100, eight exemplary recorded reflected waveforms are presented herein. Referring to FIGS. 1, 4, 5A, and 5B, at step 104, a plurality of reflected waveforms 200 at varying wellbore depths are recorded, such as by using cement bonding logging tool 14 (FIG. 3). FIG. 5A is a graph of four recorded waveforms 200a at four different depths taken in a shallower section 13a of wellbore 13 characterized by free, or unbonded, pipe, and FIG. 5B is a graph of four recorded waveforms 200b at four different depths taken in a deeper section 13b of wellbore 13 characterized by bonded pipe. It can be seen that there is a different waveform response at the free pipe zone and the bonded pipe zone. In the free pipe zone 13a, the amplitude of waveforms 200a are high. Because cement 20 attenuates the waves in bonded section 13b, waveforms 200b are characterized by a lower amplitude. The increased amplitude of waveforms 200b to the right of the chart are attributable to the response of formation 21.

Figure 6:
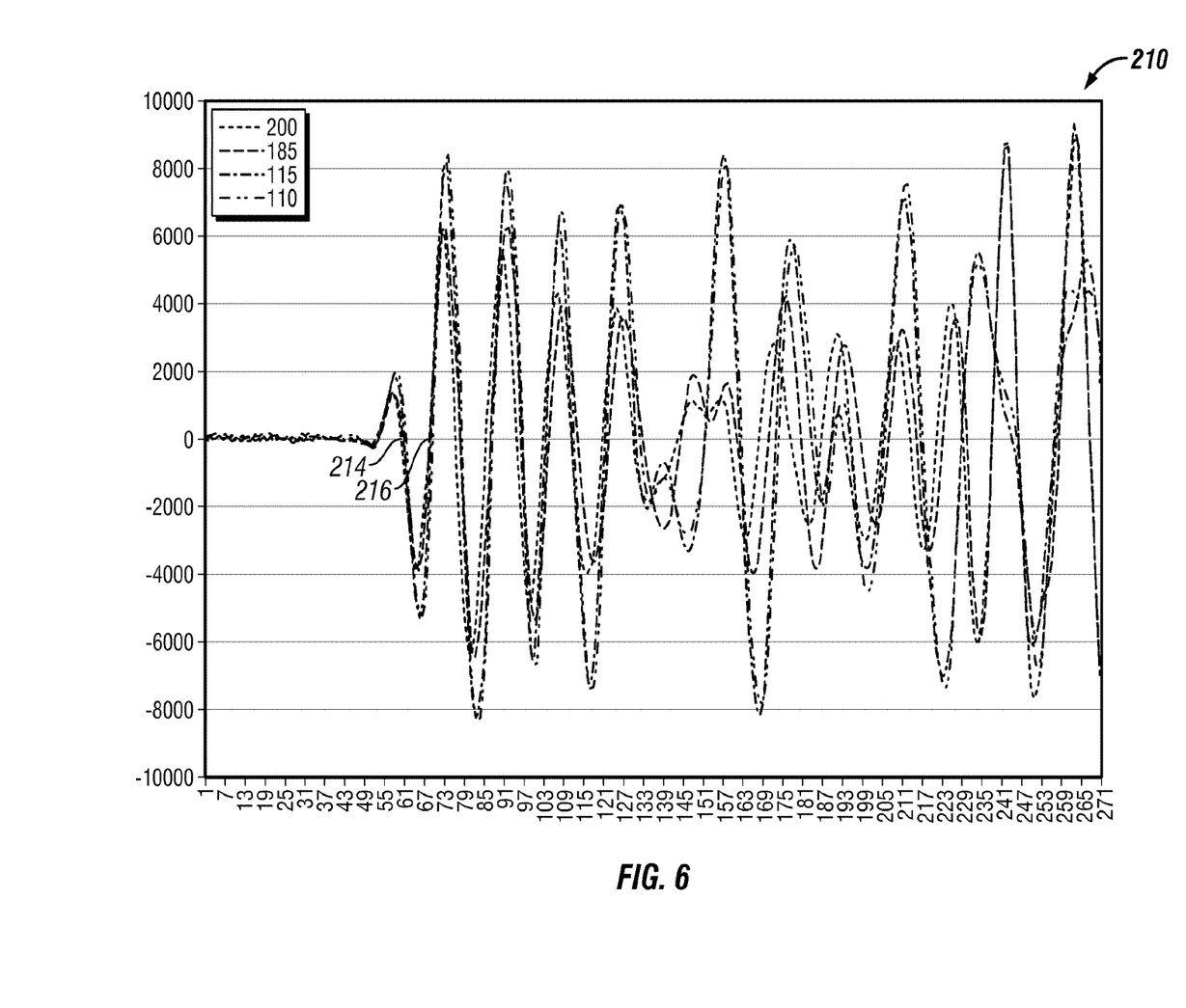
FIG. 6 is a graph showing the mathematical derivative plots of each waveform of FIG. 5A for determining minima and maxima according to an embodiment.

At step 108, for each of the recorded waveforms 200, location of amplitude maxima and minima, or peaks and troughs, are identified. According to an embodiment, maxima and minima are identified by taking the mathematical derivative of each waveform 200. FIG. 6 is a graph showing the mathematical derivative plots 210 of each waveform 200a of FIG. 5A. Each instance where derivative plot 210 changes sign corresponds to a peak or trough of the corresponding waveform 200a. Two such points 214, 216 are labeled on FIG. 6 for illustration, which correspond to peaks 204 and troughs 206 of waveforms 200a. Although not illustrated directly, the same procedure is performed with each waveform 200b of FIG. 5B.

Figure 7A:
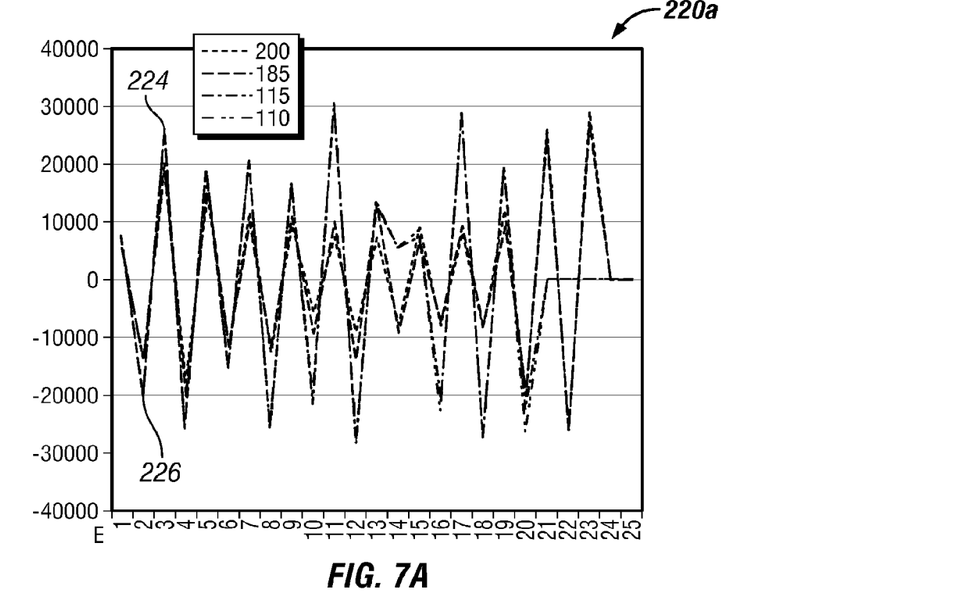
FIG. 7A is a plot of the magnitudes of the peaks and troughs of the four recorded waveforms of FIG. 5A.
Figure 7B:
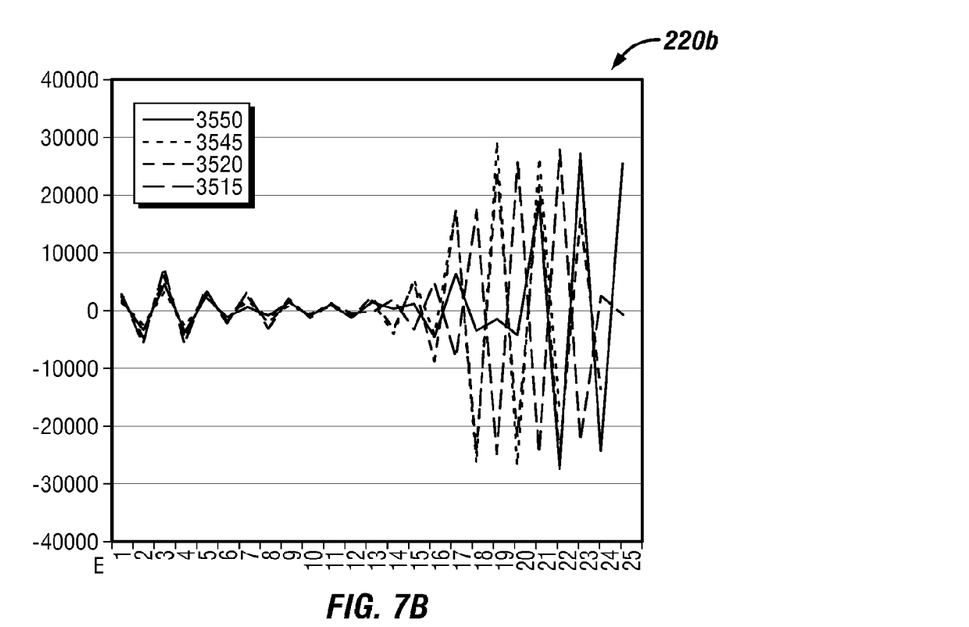
FIG. 7B is a plot of the magnitudes of the peaks and troughs of the four recorded waveforms of FIG. 5B.
Figure 8A:
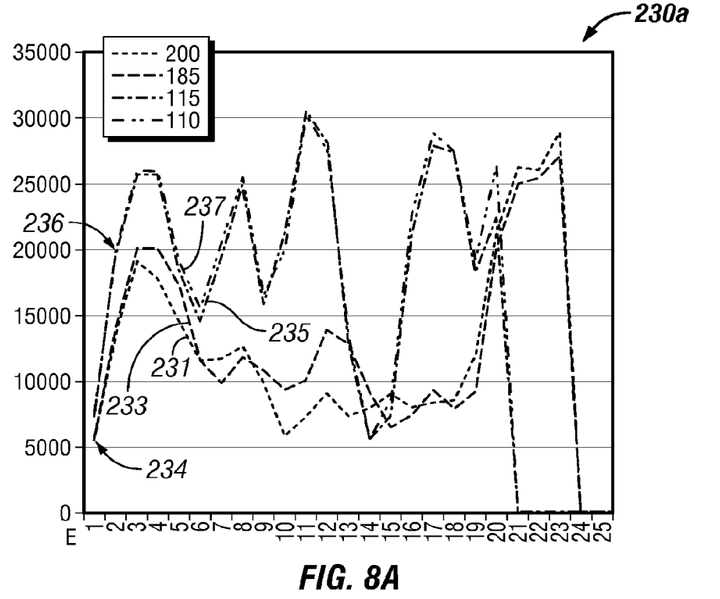
FIG. 8A is a plot of the absolute values of the magnitudes of the peaks and troughs of the four recorded waveforms of FIG. 5A.
Figure 8B:
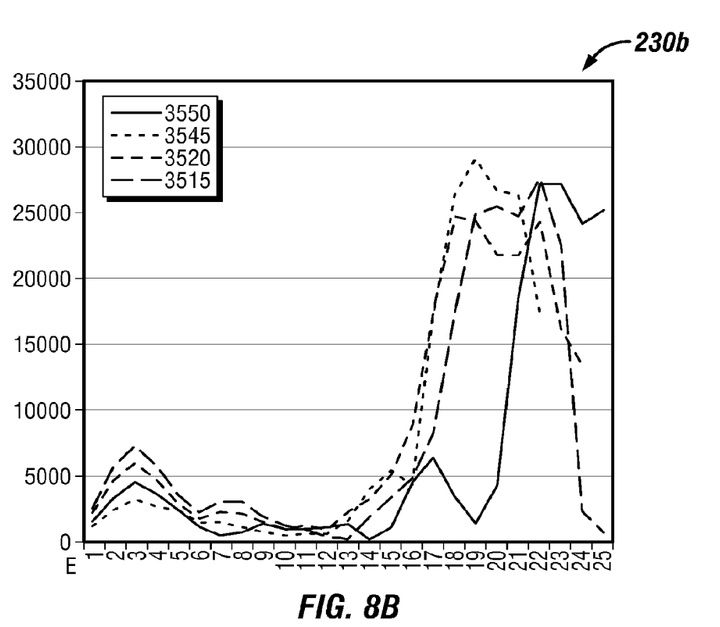
FIG. 8B is a plot of the absolute values of the magnitudes of the peaks and troughs of the four recorded waveforms of FIG. 5B.

At step 112, for each maxima and minima identified in step 108, the absolute values of the amplitudes of waveforms 200 are identified. Step 112 is illustrated in two stages. FIGS. 7A and 7B are plots of the magnitudes 220 of the peaks and troughs of waveforms 200a, 200b of FIGS. 5A, 5B, respectively. The time value corresponding to each identified maxima and minima (e.g., points 214, 216 of FIG. 6) are used to extract the magnitude values of waveforms 200 at the same times. However, magnitudes are plotted as a numbered series of points (E1, E2 . . . En) rather than based on the timescale where E1 corresponds to the amplitude of the first arrival. For example, magnitude values 224, 226 correspond to peaks 204 and troughs 206 of waveforms 200a. As shown, the magnitude points 220 may be connected by straight lines to aid viewing. The second stage of step 112 is illustrated by FIGS. 8A and 8B, which are plots of the absolute values 230 of the magnitude values 220. For example, absolute value points 234 and 236 correspond to magnitude values 224, 226 of FIG. 7A. Again, the absolute value points 230 may be connected by straight lines to aid viewing. By using absolute values, both the positive and negative peaks of the entire waveform 220 are considered together in a simplified manner.

Figure 9A:
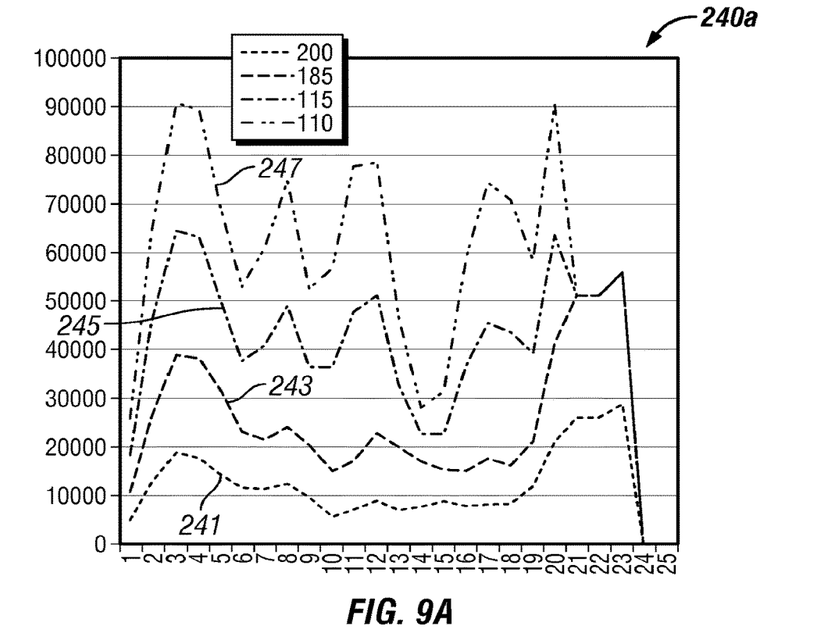
FIG. 9A is a plot of superpositioned points of the absolute value points of FIG. 8A.
Figure 9B:
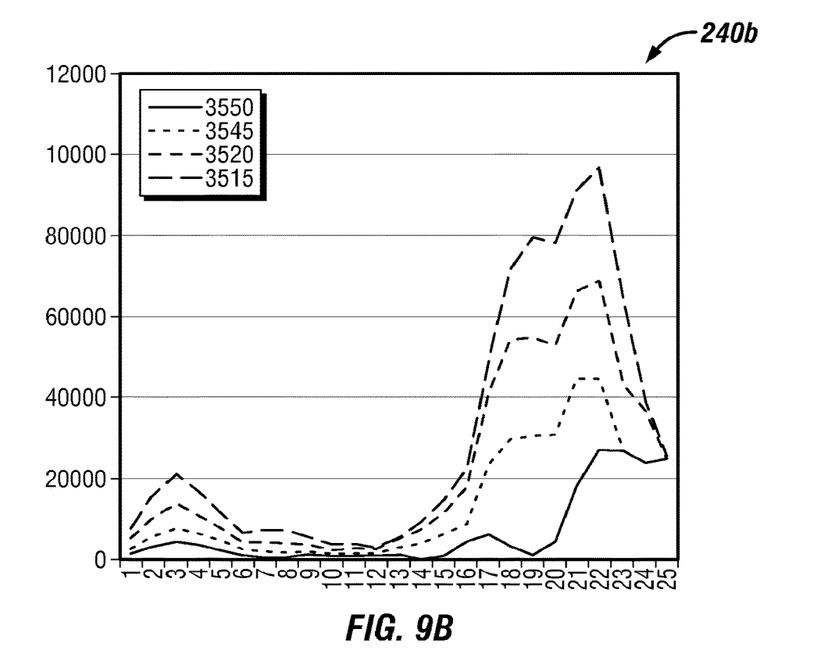
FIG. 9B is a plot of superpositioned points of the absolute value points of FIG. 8B.

From FIGS. 8A and 8B, it is possible to identify some general trends in the data of each waveform 229, and various natural groupings or sections appear. However, it is possible to stack, or superposition, the absolute value points 230 to further highlight these groupings. FIGS. 9A and 9B illustrate this step. FIGS. 9A and 9B are plots of superpositioned points 240 of the absolute value points 230 of FIGS. 8A and 8B. For example, a first series 241 of absolute value magnitudes 240a of FIG. 9A is the same as series 231 of FIG. 8A. A second series 243 of absolute value magnitudes 240a of FIG. 9A is the summation of corresponding absolute value magnitudes 230a of series 231 and 233 of FIG. 8A. A third series 245 of absolute value magnitudes 240a of FIG. 9A is the summation of corresponding absolute value magnitudes 230a of series 231, 233 and 235 of FIG. 8A. Likewise, the fourth series 247 of absolute value magnitudes 240a of FIG. 9A is the summation of corresponding absolute value magnitudes 230a of series 231, 233, 235, and 237 of FIG. 8A. FIG. 9B is generated from FIG. 8B in the same manner. The order in which the absolute value magnitudes are stacked is not critical, as it just serves to highlight natural trends in the data.

Using the above sequence of steps 104, 108, 112, various patterns begin to emerge from both the free and bonded sections 13a, 13b of wellbore 13. A routineer in the field will recognize that there are four or more distinct areas, breaks, or zones in the waveform response. Accordingly, at step 116, is analyzed and sorted based according to these naturally occurring divisions. Each zone can be adjusted or shifted based on the waveform response, casing size, casing weight, cement properties and other environmental conditions of the well. In the example of the present disclosure five zones are evident, but a greater or lesser number of zones may be appropriate for a given set of waveforms.

Figure 10:
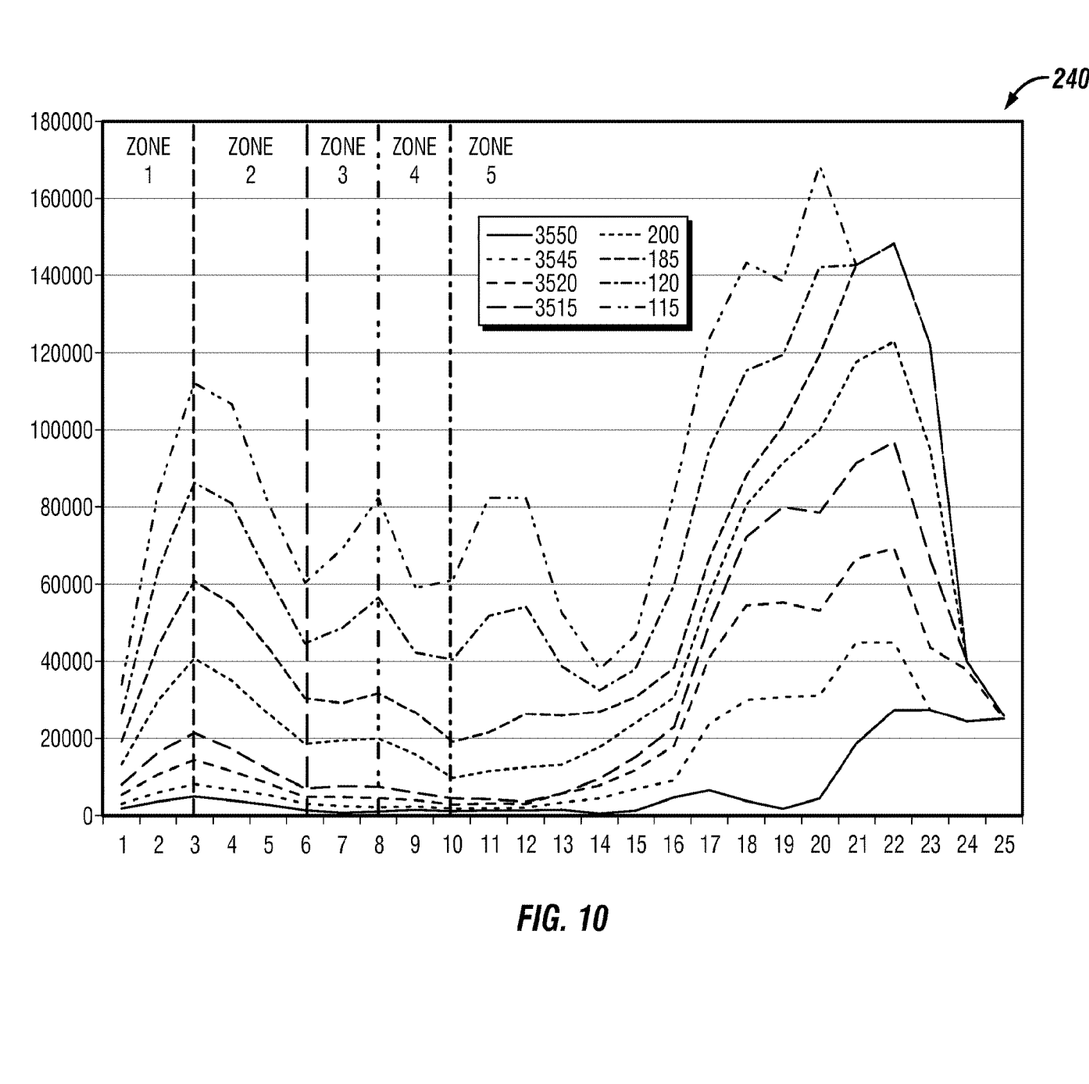
FIG. 10 is a combined plot of all eight series of superpositioned absolute value magnitudes of FIGS. 9A and 9B, showing the data divided according to naturally occurring zones.

FIG. 10 is a combined plot of all eight series of stacked absolute value magnitudes 240 of FIGS. 9A and 9B. The vertical lines show where an analyst may examine the waveform response data and divide the series of points into four or more zones according to step 116. It will be apparent to a routineer that Zone 1 corresponds to casing arrivals, and Zone 5 corresponds to formation arrivals. Zones 2-4 therefore encompass the annular area between the casing and the formation, with Zones 2 and 4 being somewhat influenced by the casing and formation, respectfully. The grouping of zones may be a function of environmental and tool conditions.

Once the zones are selected at step 116, the average amplitude for each zone for zone is determined at step 120. In an embodiment, the average amplitude of the of Zone 1 peaks are calculated twice, once with the 1st peak (E1) and once without. Because E1 values are inherently smaller than E3 values, removing the first set of values from the calculation of the arithmetic mean allows easier comparison of Zone 1 to the other zones.

According to prior art methods, pipe amplitude is calculated from the amplitude of the E1 arrival and then normalized to a certain value based on casing size and weight. However with peak analysis method 100 according to one or more embodiments, the E1 arrival data is not used. Accordingly, the waveform data is not normalized to a certain value for pipe size and weight but rather is normalized to the free pipe value for the casing in question. Thus, the highest amplitude of Zone 1 is determined to be 100% free (assuming that there is a free pipe section), and all the other amplitudes for the other zones are normalized accordingly. In other words, the end result of the above-described steps is a number different amplitude curves determined by the natural break in the waveform response and normalized to a free pipe value of unity. Although not strictly required, such normalization allows comparison of the waveform responses to a known point of reference.

Figure 11A:
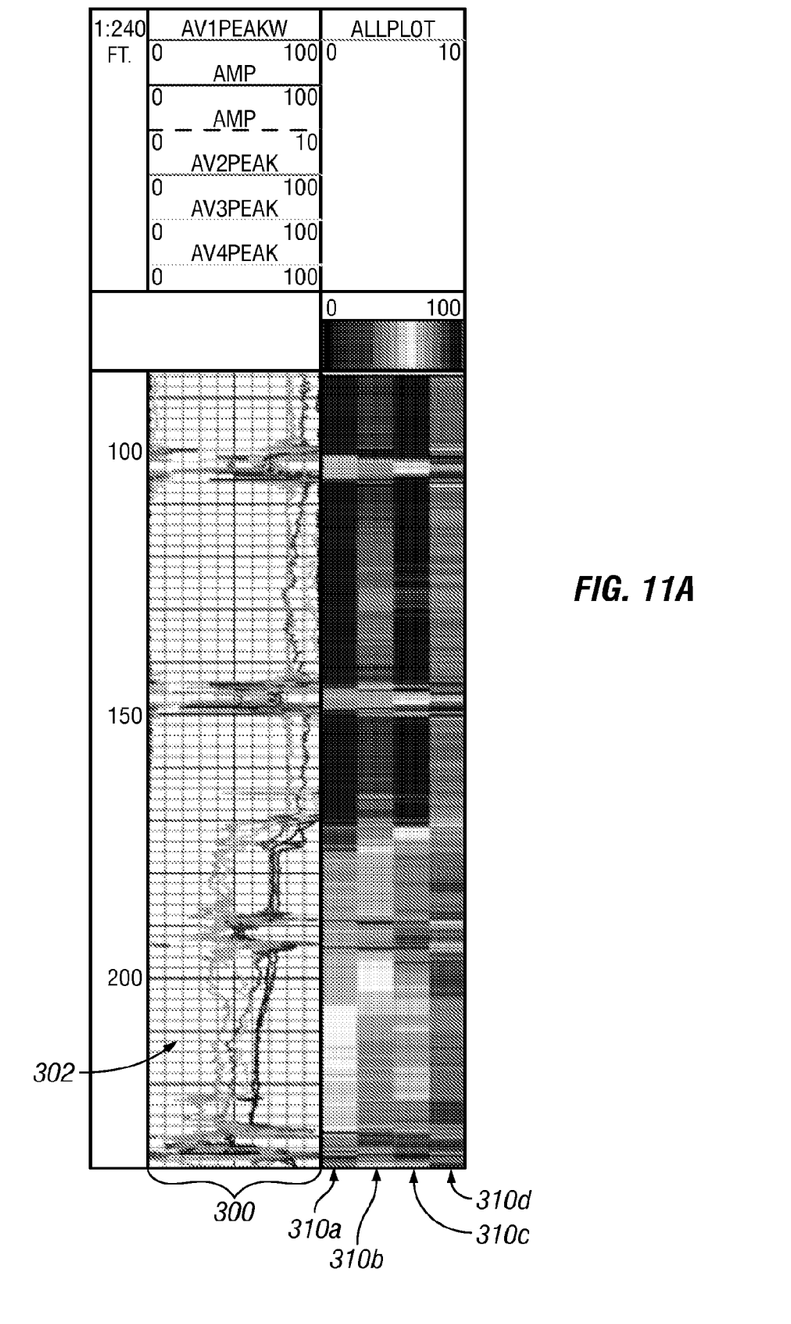
FIG. 11A is a plot of the absolute value magnitudes of FIG. 9A averaged according the zones of FIG. 10, shown both as amplitude curves versus depth and as color- or intensity-maps versus depth.
Figure 11B:
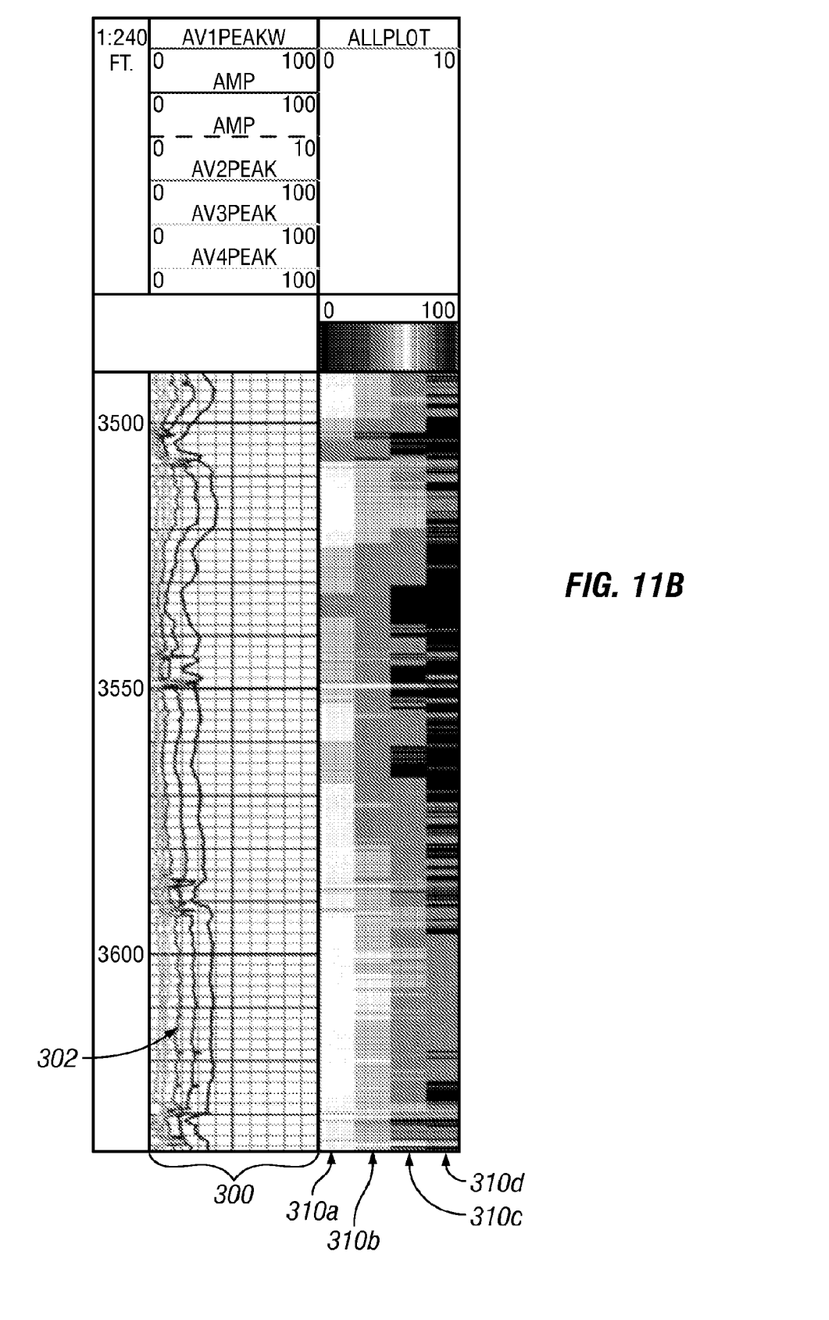
FIG. 11B is a plot of the absolute value magnitudes of FIG. 9B averaged according to the zones of FIG. 10, shown both as amplitude curves versus depth and as color- or intensity-maps versus depth.

The average amplitudes for each zone, whether normalized or not, indicate a quality of cement bonding. However, to make the data easier to understand, a plot with color, gray scale, or intensity mapping may be used to visually show the amplitude values of each zone with depth. For example, colors may be used ranging from a black for low amplitudes grading to lighter colors then finally to a light blue which grades to a dark blue at 100percent free pipe amplitude. A cutoff value between the cement spectrum and the free pipe spectrum may be assigned based on the interpretation and experience. FIGS. 11A and 11B illustrate such a plot. FIGS. 11A and 11B are plots of the absolute value magnitudes of FIGS. 9A and 9B, respectively, averaged according the zones of FIG. 10.

FIGS. 11A and 11B show the zonal averaged absolute value magnitude data, both as amplitude curves versus depth and as color- or intensity-maps versus depth. A left-hand graph 300 includes four amplitude curves 302 (labeled AV1PEAKW, AV2PEAK, AV3PEAK, AV4PEAK) of the zonal averaged absolute value magnitude data versus depth. To the immediate right of graph 300, curves 302 are re-plotted as color- or intensity-maps 310a-310d, which show the color coding of the above curves in the same order, with a scale from 0to 100, versus depth. The darker colors indicate good bond, ranging to poor bond as indicated by the dark blue. Other color schemes, including grayscale or pixilation, may be used as appropriate.

Using the normalization of the amplitude of the waveform peaks allow quick and useful examination of the waveform, and in turn the evaluation of annular material. Separating the waveform peaks into four or more distinctive zones based on slope changes and color-mapping the zones allows quick and useful analysis. These waveforms and analysis are only mildly influenced by the user picks, thus eliminating possible errors typical found in cement evaluation. As each zone is influenced by its surrounding material, Zones 2 and 3 provide detailed data regarding of the material in the annular space. The amplitude of each zone is determined, and the plots easier to evaluate and explain than previous methods. Accordingly, peak analysis method 100 takes the guess work out of the examining the sonic, pulse echo ultrasonic, and the pitch and catch waveforms, and applies standard methods of using amplitude data to evaluate the cement sheath. High amplitudes indicate free pipe while lower amplitudes indicated dampening of the waveform, which is common with cement slurries.

In summary, a cement bond log from recorded ultrasonic first and second waveforms, a method for evaluating bonding of cement in a wellbore between a casing and a wellbore wall, and a method for creating a cement bond log from recorded ultrasonic first and second waveforms have been described. Embodiments of the cement bond log may generally have: A first mean value of absolute value amplitudes of an ultrasonic first waveform at minima and maxima of the first waveform corresponding with casing arrival data; a second mean value of absolute value amplitudes of the first waveform at minima and maxima of the first waveform corresponding with inner annular data; a third mean value of absolute value amplitudes of the first waveform at minima and maxima of the first waveform corresponding with outer annular data; a fourth mean value of absolute value amplitudes of the first waveform at minima and maxima of the first waveform corresponding with wellbore wall arrival data; a first mean value of absolute value amplitudes of an ultrasonic second waveform at minima and maxima of the second waveform corresponding with casing arrival data; a second mean value of absolute value amplitudes of the second waveform at minima and maxima of the second waveform corresponding with inner annular data; a third mean value of absolute value amplitudes of the second waveform at minima and maxima of the second waveform corresponding with outer annular data; and a fourth mean value of absolute value amplitudes of the second waveform at minima and maxima of the second waveform corresponding with wellbore wall arrival data. Embodiments of the method for evaluating bonding of cement in a wellbore may generally include: Disposing a logging tool within the wellbore; transmitting by the logging tool an ultrasonic wave at a first wellbore depth; receiving by the logging tool a reflected ultrasonic wave at the first depth; recording a first waveform as a function of amplitude and time of the received reflected ultrasonic wave at the first depth; transmitting by the logging tool an ultrasonic wave at a second wellbore depth; receiving by the logging tool a reflected ultrasonic wave at the second depth; recording a second waveform as a function of amplitude and time of the received reflected ultrasonic wave at the second depth; identifying a first series of points corresponding to maxima and minima of the first waveform; identifying absolute value amplitudes of the first waveform at the first series of points; identifying a second series of points corresponding to maxima and minima of the second waveform; identifying absolute value amplitudes of the second waveform at the second series of points; analyzing a correlation of the absolute value amplitudes of the first waveform at the first series of points with the absolute value amplitudes of the second waveform at the second series of points to divide the first and second series of points into at least first, second, third, and fourth zones; and calculating first, second, third, and fourth mean values of the absolute value amplitudes of the first waveform for points of the first series of points falling within each of the first, second, third, and fourth zones, respectively; wherein the first, second, third, and fourth mean values of the absolute value amplitudes of the first waveform relate to cement bonding at the first depth. Embodiments of the method for creating a cement bond log may generally include: Identifying a first series of points corresponding to maxima and minima of the first waveform; identifying absolute value amplitudes of the first waveform at the first series of points; identifying a second series of points corresponding to maxima and minima of the second waveform; identifying absolute value amplitudes of the second waveform at the second series of points; analyzing a correlation of the absolute value amplitudes of the first waveform at the first series of points with the absolute value amplitudes of the second waveform at the second series of points to divide the first and second series of points into at least first, second, third, and fourth zones; calculating first, second, third, and fourth mean values of the absolute value amplitudes of the first waveform for points of the first series of points falling within each of the first, second, third, and fourth zones, respectively; and plotting the magnitudes of the first, second, third, and fourth mean values of the absolute value amplitudes of the first waveform for points of the first series of points falling within each of the first, second, third, and fourth zones, respectively, as a function of color or intensity.

Any of the foregoing embodiments may include any one of the following elements or characteristics, alone or in combination with each other: The magnitudes of the first, second, third, and fourth mean values of the absolute value amplitudes of the first waveform are plotted as a function of color; the magnitudes of the first, second, third, and fourth mean values of the absolute value amplitudes of the second waveform are plotted as a function of color; the magnitudes of the first, second, third, and fourth mean values of the absolute value amplitudes of the first waveform are plotted as a function of intensity; the magnitudes of the first, second, third, and fourth mean values of the absolute value amplitudes of the second waveform are plotted as a function of intensity; the first zone is determined so as to correspond with casing arrival data; the second and third zones are determined so as to correspond to inner and outer annular data, respectively; the fourth zone is determined so as to correspond with wellbore wall arrival data; calculating first, second, third, and fourth mean values of the absolute value amplitudes of the second waveform for points of the second series of points falling within each of the first, second, third, and fourth zones, respectively; the first, second, third, and fourth mean values of the absolute value amplitudes of the second waveform relate to cement bonding at the second depth; calculating a mathematical derivative of the first waveform to identify the first series of points; calculating a mathematical derivative of the second waveform to identify the second series of points; plotting the magnitudes of the first, second, third, and fourth mean values of the absolute value amplitudes of the first waveform as a function of color or intensity; plotting the magnitudes of the first, second, third, and fourth mean values of the absolute value amplitudes of the second waveform as a function of color or intensity; plotting on a first graph the first, second, third, and fourth mean values of the absolute value amplitudes of the first waveform; plotting on the first graph respective summations of the first, second, third, and fourth mean values of the absolute value amplitudes of the first waveform and the first, second, third, and fourth mean values of the absolute value amplitudes of the second waveform; analyzing the correlation using the first graph; normalizing the first, second, third, and fourth mean values of the absolute value amplitudes of the first waveform so that the first mean value of the absolute value amplitudes of the first waveform equals a unity free pipe value; normalizing the first, second, third, and fourth mean values of the absolute value amplitudes of the second waveform so that the first mean value of the absolute value amplitudes of the second waveform equals the unity free pipe value; plotting the magnitudes of the normalized first, second, third, and fourth mean values of the absolute value amplitudes of the first waveform as a function of color or intensity; and plotting the magnitudes of the normalized first, second, third, and fourth mean values of the absolute value amplitudes of the second waveform as a function of color or intensity.

While various embodiments have been illustrated in detail, the disclosure is not limited to the embodiments shown. Modifications and adaptations of the above embodiments may occur to those skilled in the art. Such modifications and adaptations are in the spirit and scope of the disclosure.

What is claimed:

1. A method for evaluating bonding of cement in a wellbore between a casing and a wellbore wall, comprising:
   disposing a logging tool within said wellbore;
   transmitting by said logging tool an ultrasonic wave at a first wellbore depth;
   receiving by said logging tool a reflected ultrasonic wave at said first depth;
   recording a first waveform as a function of amplitude and time of said received reflected ultrasonic wave at said first depth;
   transmitting by said logging tool an ultrasonic wave at a second wellbore depth;

receiving by said logging tool a reflected ultrasonic wave at said second depth;

recording a second waveform as a function of amplitude and time of said received reflected ultrasonic wave at said second depth;

identifying first maxima and minima of said first waveform in relation to time;

using first time values corresponding to said first maxima and minima, extracting first absolute value amplitudes of said first waveform at said first time values;

plotting said first absolute value amplitudes as a first series of points;

identifying second maxima and minima of said second waveform in relation to time;

using second time values corresponding to said second maxima and minima, extracting second absolute value amplitudes of said second waveform at said second time values;

plotting said second absolute value amplitudes as a second series of points;

analyzing a correlation of said first absolute value amplitudes at said first series of points with said second absolute value amplitudes at said second series of points to divide said first and second series of points into at least first, second, third, and fourth zones;

calculating first, second, third, and fourth mean values of said first absolute value amplitudes for points of said first series of points falling within each of said first, second, third, and fourth zones, respectively;

wherein the first, second, third, and fourth mean values of said first absolute value amplitudes relate to cement bonding at said first depth;

plotting the magnitudes of said first, second, third, and fourth mean values of said first absolute value amplitudes as a function of color or intensity, and plotting the magnitudes of said first, second, third, and fourth mean values of said second absolute value amplitudes as a function of color or intensity, thereby generating a cement bond log; and using the cement bond log to evaluate bonding of the cement in the wellbore between the casing and wellbore wall.

2. The method of claim 1 wherein:

said first zone is determined so as to correspond with casing arrival data;

said second and third zones are determined so as to correspond to inner and outer annular data, respectively; and said fourth zone is determined so as to correspond with wellbore wall arrival data.

3. The method of claim 2 further comprising:

normalizing said first, second, third, and fourth mean values of said first absolute value amplitudes so that said first mean value of said first absolute value amplitudes equals a unity free pipe value; and normalizing said first, second, third, and fourth mean values of said second absolute value amplitudes so that said first mean value of said second absolute value amplitudes equals said unity free pipe value.

4. The method of claim 3 further comprising:

plotting the magnitudes of said normalized first, second, third, and fourth mean values of said first absolute value amplitudes as a function of color or intensity; and plotting the magnitudes of said normalized first, second, third, and fourth mean values of said second absolute value amplitudes as a function of color or intensity.

5. The method of claim 1 further comprising:

calculating first, second, third, and fourth mean values of said second absolute value amplitudes for points of said second series of points falling within each of said first, second, third, and fourth zones, respectively; wherein the first, second, third, and fourth mean values of said second absolute value amplitudes relate to cement bonding at said second depth.

6. The method of claim 1 further comprising:

calculating a mathematical derivative of said first waveform to identify said first series of points; and calculating a mathematical derivative of said second waveform to identify said second series of points.

7. The method of claim 1 further comprising:

plotting on a first graph said first, second, third, and fourth mean values of said first absolute value amplitudes; and plotting on said first graph respective summations of said first, second, third, and fourth mean values of said first absolute value amplitudes and said first, second, third, and fourth mean values of said second absolute value amplitudes; and then analyzing said correlation using said first graph.

8. A method for creating a cement bond log from recorded ultrasonic first and second waveforms, comprising:

identifying first maxima and minima of said first waveform in relation to time;

using first time values corresponding to said first maxima and minima, extracting first absolute value amplitudes at said first time values;

plotting said first absolute value amplitudes as a first series of points;

identifying second maxima and minima of said second waveform in relation to time;

using second time values corresponding to said second maxima and minima, extracting second absolute value amplitudes at said second time values;

plotting said second absolute value amplitudes as a second series of points;

analyzing a correlation of said first absolute value amplitudes at said first series of points with said second absolute value amplitudes at said second series of points to divide said first and second series of points into at least first, second, third, and fourth zones;

calculating first, second, third, and fourth mean values of said first absolute value amplitudes for points of said first series of points falling within each of said first, second, third, and fourth zones, respectively; and plotting the magnitudes of said first, second, third, and fourth mean values of said first absolute value amplitudes for points of said first series of points falling within each of said first, second, third, and fourth zones, respectively, as a function of color or intensity, thereby creating the cement bond log.

9. The method of claim 8 wherein:

said first zone is determined so as to correspond with casing arrival data;

said second and third zones are determined so as to correspond to inner and outer annular data, respectively; and said fourth zone is determined so as to correspond with wellbore wall arrival data.

10. The method of claim 9 further comprising:

normalizing said first, second, third, and fourth mean values of said first absolute value amplitudes so that said first mean value of said first absolute value amplitudes equals a unity free pipe value; and normalizing said first, second, third, and fourth mean values of said second absolute value amplitudes so that said first mean value of said second absolute value amplitudes equals said unity free pipe value.

11. The method of claim 10 further comprising:
plotting the magnitudes of said normalized first, second, third, and fourth mean values of said first absolute value amplitudes as a function of color or intensity; and
plotting the magnitudes of said normalized first, second, third, and fourth mean values of said second absolute value amplitudes as a function of color or intensity.

12. The method of claim 8 further comprising:
calculating first, second, third, and fourth mean values of said second absolute value amplitudes for points of said second series of points falling within each of said first, second, third, and fourth zones, respectively; and
plotting the magnitudes of said first, second, third, and fourth mean values of said second absolute value amplitudes for points of said second series of points falling within each of said first, second, third, and fourth zones, respectively, as a function of color or intensity.

13. The method of claim 8 further comprising:
calculating a mathematical derivative of said first waveform to identify said first series of points; and
calculating a mathematical derivative of said second waveform to identify said second series of points.

14. The method of claim 8 further comprising:
plotting on a first graph said first, second, third, and fourth mean values of said first absolute value amplitudes for points of said first series of points falling within each of said first, second, third, and fourth zones, respectively; and
plotting on said first graph respective summations of said first, second, third, and fourth mean values of said first absolute value amplitudes for points of said first series of points falling within each of said first, second, third, and fourth zones, respectively, and said first, second, third, and fourth mean values of said second absolute value amplitudes for points of said second series of points falling within each of said first, second, third, and fourth zones, respectively; and then
analyzing said correlation using said first graph.

* * * * *